(12) United States Patent
Rife

(10) Patent No.: US 7,159,590 B2
(45) Date of Patent: Jan. 9, 2007

(54) TRACHEA TUBE WITH GERMICIDAL LIGHT SOURCE

(76) Inventor: Robert W. Rife, 1513 Pine Island View, Mt. Pleasant, SC (US) 29464

( * ) Notice: Subject to any disclaimer, the term of this patent is extended or adjusted under 35 U.S.C. 154(b) by 0 days.

(21) Appl. No.: 11/017,243

(22) Filed: Dec. 20, 2004

(65) Prior Publication Data

US 2006/0130846 A1    Jun. 22, 2006

(51) Int. Cl.
*A61M 16/00* (2006.01)
(52) U.S. Cl. .................. 128/207.15; 128/207.14; 128/200.26
(58) Field of Classification Search .......... 128/200.26, 128/207.14, 207.15, 207.16, 909, 912, 200.24; 250/455.1
See application file for complete search history.

(56) References Cited

U.S. PATENT DOCUMENTS

| | | | | |
|---|---|---|---|---|
| 5,053,033 A | * | 10/1991 | Clarke | 606/3 |
| 5,065,757 A | * | 11/1991 | Dragisic et al. | 128/207.14 |
| 5,165,395 A | * | 11/1992 | Ricci | 128/202.22 |
| 5,193,544 A | * | 3/1993 | Jaffe | 600/323 |
| 5,260,020 A | * | 11/1993 | Wilk et al. | 422/22 |
| 5,507,284 A | * | 4/1996 | Daneshvar | 128/207.14 |
| 5,522,868 A | | 6/1996 | Buckley et al. | |
| 5,637,877 A | * | 6/1997 | Sinofsky | 250/492.1 |
| 5,653,683 A | | 8/1997 | D'Andrea | |
| 5,695,482 A | * | 12/1997 | Kaldany | 604/526 |
| 5,762,638 A | | 6/1998 | Shikani et al. | |
| 5,855,203 A | * | 1/1999 | Matter | 128/207.14 |
| 5,891,082 A | | 4/1999 | Leone et al. | |
| 6,443,147 B1 | * | 9/2002 | Matter | 128/200.26 |
| 6,464,625 B1 | | 10/2002 | Ganz | |
| 6,470,888 B1 | * | 10/2002 | Matter | 128/207.14 |
| 6,491,618 B1 | | 12/2002 | Ganz | |
| 6,551,346 B1 | * | 4/2003 | Crossley | 607/88 |
| 2001/0049464 A1 | | 12/2001 | Ganz | |
| 2002/0074559 A1 | | 6/2002 | Dowling et al. | |
| 2003/0191459 A1 | | 10/2003 | Ganz et al. | |
| 2004/0158302 A1 | | 8/2004 | Chornenky et al. | |

FOREIGN PATENT DOCUMENTS

GB      2 364 622 A     1/2002
WO     WO 99/53966     10/1999

* cited by examiner

*Primary Examiner*—Justine R. Yu
*Assistant Examiner*—Annette Dixon
(74) *Attorney, Agent, or Firm*—B. Craig Killough; Ernest B. Lipscomb, III

(57) ABSTRACT

A tube for insertion into a trachea having a germicidal light source that is positioned above a cuff that holds the tube in place in the trachea. Activation of the germicidal light source causes an radiation emission that kills undesired bacteria that is fostered by the tube and the cuff, reducing the patient's risk of associated disease, and reducing the need for antibiotics.

15 Claims, 5 Drawing Sheets

TRACHEA TUBE WITH GERMICIDAL LIGHT SOURCE

FIELD OF THE INVENTION

This invention relates to tubes for medical use generally, and is more specifically related to a tube for insertion into a trachea that incorporates a germicidal light source.

BACKGROUND

Endotracheal and tracheostomy tubes are used to provide an airway in patients who do not have an adequate airway do due to medical conditions. An endotracheal tube is inserted through the mouth and larynx and into the trachea. Tracheostomy tubes are inserted through an incision just above the sternal notch.

With both types of tubes, an inflatable cuff is incorporated at the distal end of the tube that is present within the trachea. The cuff allows pressurization of the lungs during mechanical ventilation, and prevents aspiration of oral secretions and other contaminants into the lungs. The inflated cuff also helps secure the tube in position. A consequence of the inflated cuff is that secretions pool around the top of the cuff, where undesired bacteria may colonize. Microaspiration of these secretions around the cuff is a leading cause of ventilator-associated pneumonia in this patient population.

SUMMARY OF THE PRESENT INVENTION

The present invention is a tube for insertion into a trachea. A germicidal light source is present within the chamber. The chamber is substantially transparent to the germicidal light. Activation of the germicidal light source causes a radiation emission that kills the undesired bacteria reducing the risk of pneumonia associated with aspiration of the bacteria and as a consequence may reduce the need for administration of antibiotics.

DETAILED DESCRIPTION OF THE PREFERRED EMBODIMENTS

Figure 1:
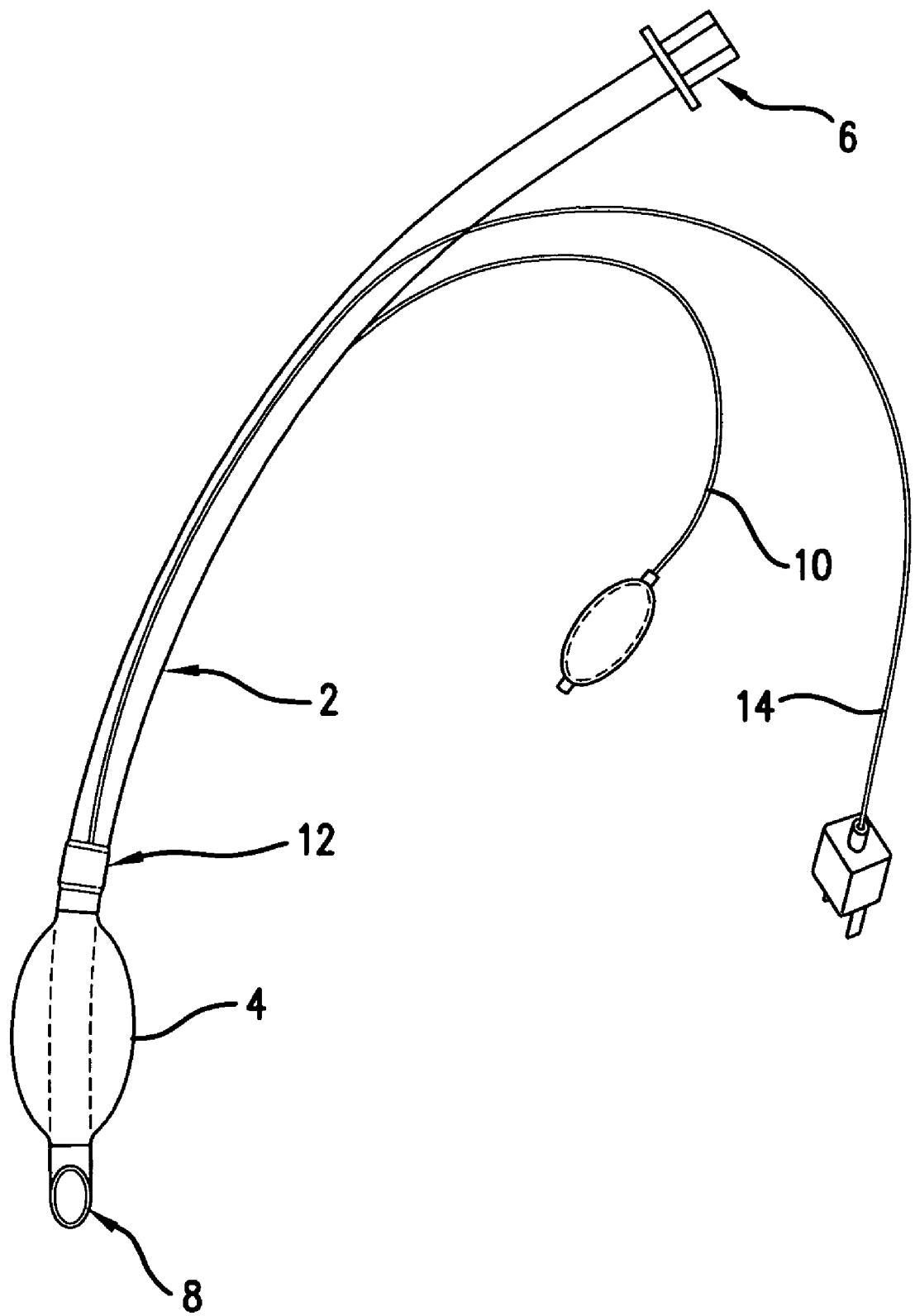
FIG. 1 shows an embodiment of the endotracheal tube of the present invention.

FIG. 1 shows an endotracheal tube 2 according to the present invention. The endotracheal tube has a cuff 4 that is present on a portion of the tube. The upper end 6 of the endotracheal tube extends out of the mouth of the patient, while the lower end opens into the trachea. The cuff is positioned just above the opening 8 of the lower end. When the tube is inserted through the mouth and into the trachea, the cuff, being of a larger dimension than the remainder of the tube, is expanded to hold the tube in place by pressure against portions of the wall of the trachea contacted by the cuff. The cuff may be expanded by inflation with air or other gases through an air supply conduit 10.

Figure 2:
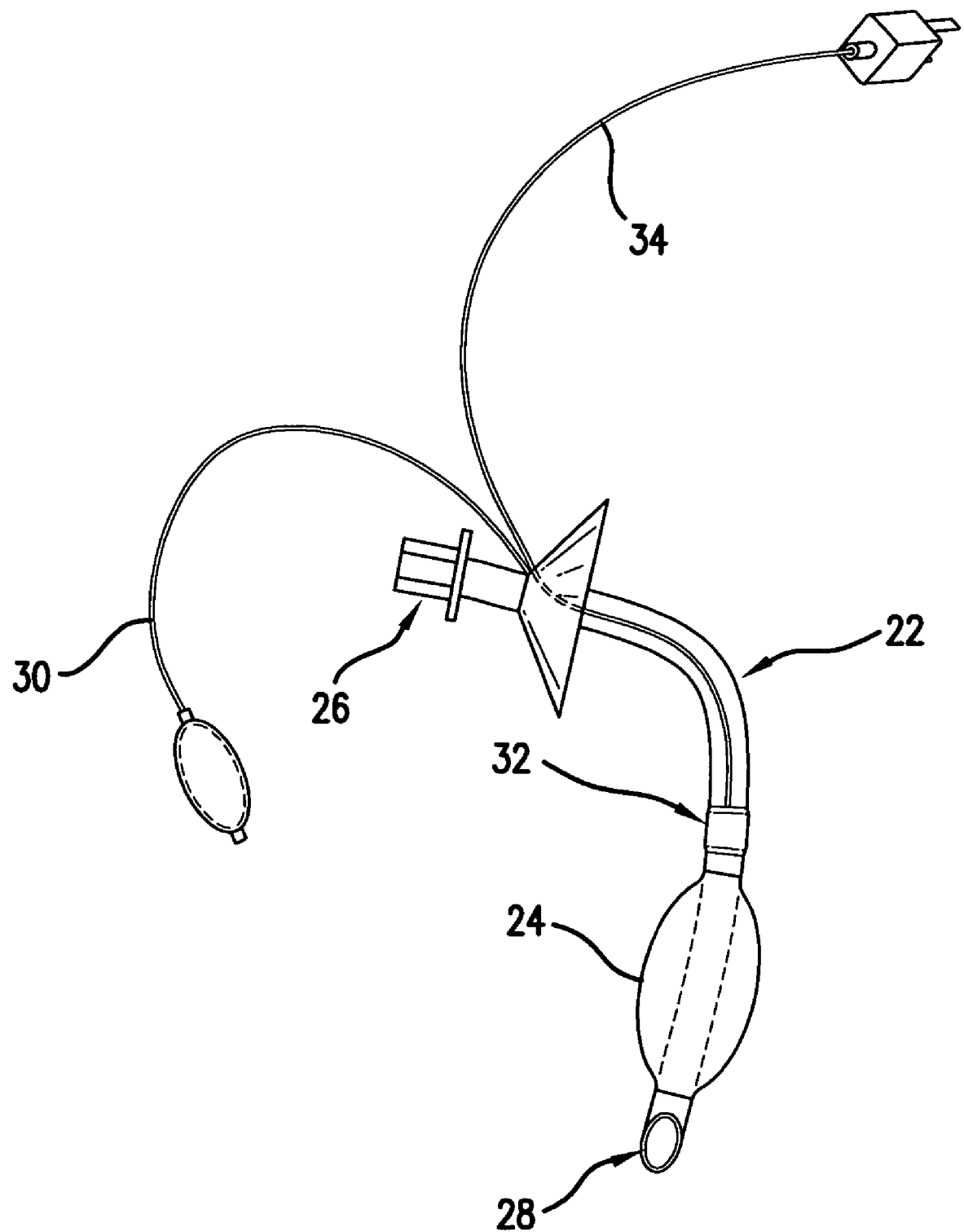
FIG. 2 shows an embodiment of the tracheostomy tube of the present invention.

The tracheostomy tube 22 shown in FIG. 2 has the same novel features and method of use as the endotracheal tube. The differences between the endotracheal tube of the preferred embodiment and the tracheostomy of the preferred embodiment are the same as the differences in the known endotracheal tubes and tracheostomy tubes.

FIG. 2 shows a tracheostomy tube 22 according to the present invention. The tracheostomy tube has a cuff 24 that is present on a portion of the tube. The upper end 26 of the tracheotomy tube extends out of an incision in the patient, while the lower end opens into the trachea. The cuff is positioned just above the opening 28 of the lower end. When the tube is inserted through the mouth and into the trachea, the cuff, being of a larger dimension than the remainder of the tube, is expanded to hold the tube in place by pressure against portions of the wall of the trachea contacted by the cuff. The cuff may be expanded by inflation with air or other gases through an air supply conduit 30.

The tube of FIGS. 1 and 2 has a chamber 12, 32 that is positioned just above the cuff. The chamber does not interfere with inflation and deflation of the cuff. A germicidal light source is present within the chamber. The chamber is preferred to be an annular member that completely surrounds the tube, with all surfaces of the chamber being smooth so as to facilitate insertion of the tube. The exterior surfaces of the chamber should not materially extend beyond the uninflated cuff, which facilitates insertion of the tube into the trachea. It is preferred that the extreme upper and extreme lower edges of the chamber are rounded or are otherwise tapered where the chamber joins the tube, so as to facilitate insertion and removal of the tube from the trachea. In summary, all of the exterior surfaces of the chamber should be smooth, with no sharp points or edges, including the edges where the chamber joins the tube.

The chamber is substantially transparent to the germicidal light. In the preferred embodiment, the germicidal light emits ultraviolet radiation, and particularly, the germicidal light emits ultraviolet C radiation (UVC), having a bandwidth that is consistent with UVC radiation. The UVC light source is contained within the chamber, and upon actuation, the chamber does not interfere with the transmission of UVC light to the exterior of the chamber. The UVC radiation is directed to, and acts upon, bacteria that are present and growing as a result of materials that are trapped within the trachea by the cuff and the tube.

Figure 3:
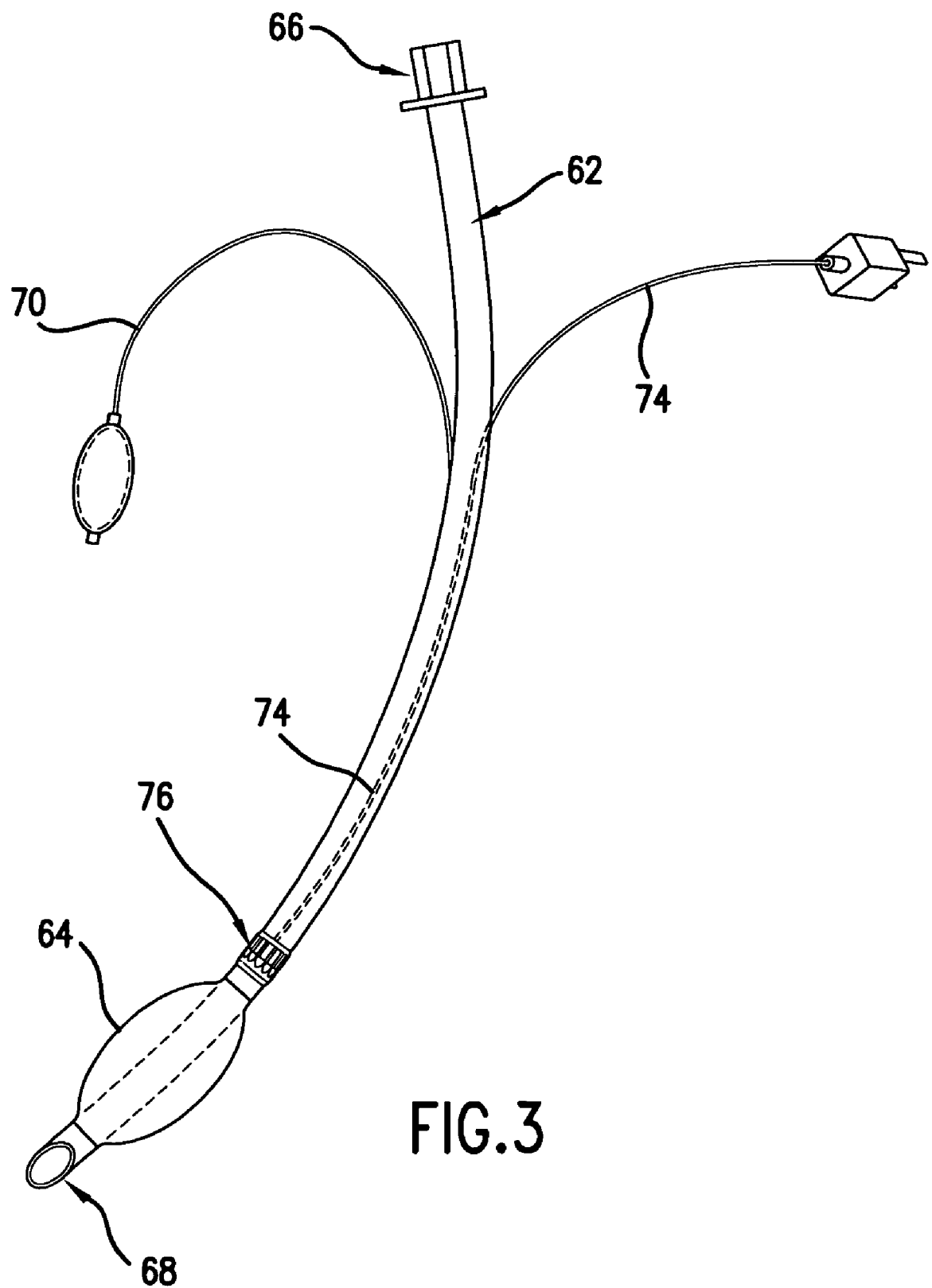
FIG. 3 shows an alternate embodiment of a tube according to the present invention.
Figure 4:
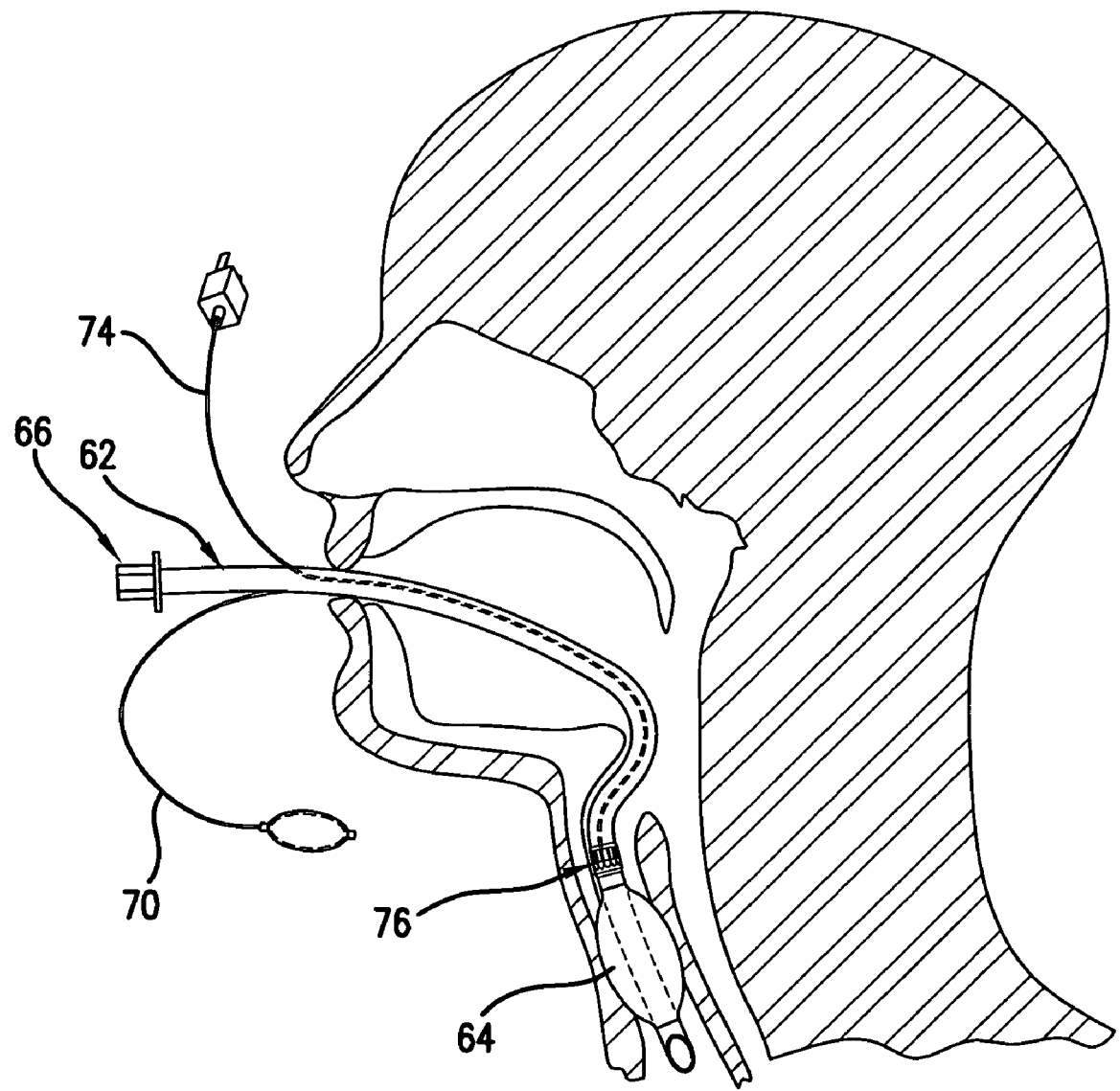
FIG. 4 shows an endotracheal tube according to the present invention in position.
Figure 5:
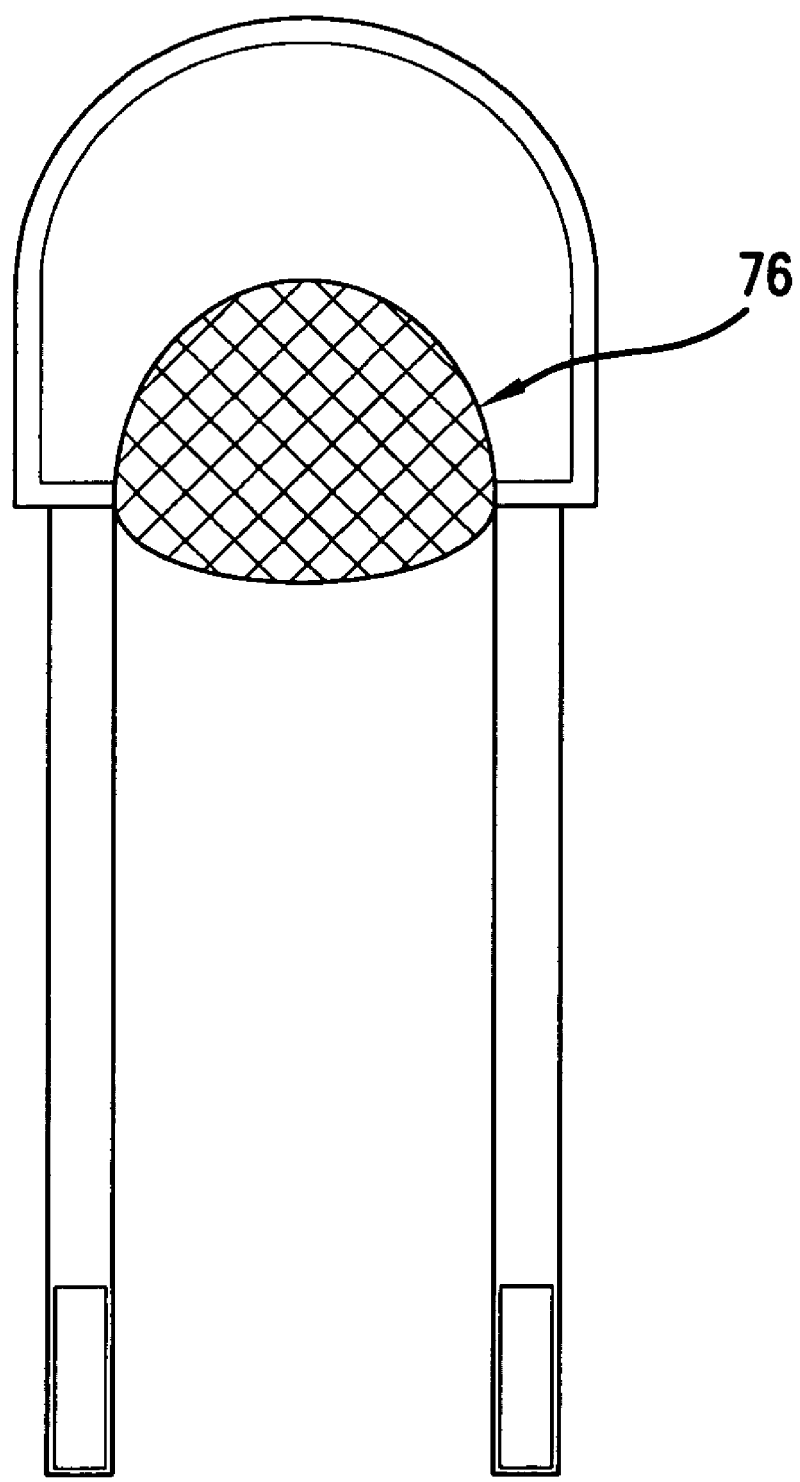
FIG. 5 is an isolation of a germicidal light emitting device.

FIG. 3 shows an additional embodiment of the endotracheal tube 62 according to the present invention. The endotracheal tube has a cuff 64 that is present on a portion of the tube. The upper end 66 of the endotracheal tube extends out of the mouth of the patient, while the lower end opens into the trachea. The cuff is positioned just above the opening 68 of the lower end. When the tube is inserted through the mouth and into the trachea, the cuff, being of a larger dimension than the remainder of the tube, is expanded to hold the tube in place by pressure against portions of the wall of the trachea contacted by the cuff. The cuff may be expanded by inflation with air or other gases through an air supply conduit 70.

The tube of FIG. 3 has a chamber 12, 32 has a ring of germicidal light emitting diodes (LEDs) 76. The LEDs are preferred to emit radiation in the ultraviolet C band. The LEDs are positioned just above the cuff, and are preferred to form an annular ring around the tube. The LEDs may be covered with a substantially clear material, which both assists in mounting the LEDs, and provides a smooth surface. A substantially transparent shrink tubing may be used, or a non toxic clear resin may be used to mount and cover the LEDs. The LED configuration of FIG. 3 may also be used in a tracheostomy tube.

In one embodiment, the chamber covering the LEDs of FIG. 3 is formed by surrounding the LEDs and the portion of the tube in which the LEDs are mounted with a section of shrink wrap tubing. The substantially transparent shrink wrap tubing is heated, the shrink wrap tubing shrinks and covers the LEDs, providing a smooth surface, while also retaining the LEDs in position on the tube.

In a preferred embodiment, a conduit 14,34,74 is provided in the tube through which an electrical current passes to provide power to the UVC light source. In particular, it is preferred that the conduit is provided in a wall of the endotracheal tube, so that the conduit does not interfere with insertion or removal of the tube. Appropriate conductors, such as wires, may be located within the conduit, and provide the appropriate current to the UVC light source. It is preferred to use a low power germicidal light source, so as to reduce the likelihood of detrimental electrical shock to the patient, in the event that a malfunction of the device occurs. In particular, it is preferred to use a direct current power source, although an alternating current power source may be used. In another embodiment, a self-contained battery could be provided with the tube. Under normal circumstances, none of the conductors will contact the patient.

It is neither necessary nor desired for the germicidal light source to operate in a steady state, but rather, operation of the germicidal light source may be intermittent. An appropriate timing circuit may be provided to periodically operate the device. Intermittent operation reduces the undesired effects of, for example, UVC radiation, and further, reduces the power requirements for the device, particularly if the device is battery operated. The period of operation may be determined according to the power output of the germicidal light, and determined by empirical study.

The invention claimed is:

1. A tube for insertion into a trachea, said tube comprising
   an elongated tube;
   an expandable cuff located on a section of said elongated tube that is expanded to hold said tube within a trachea of a user; and
   a germicidal light source positioned on said elongated tube and above said expandable cuff, wherein said germicidal light source transmits germicidal light toward said expandable cuff, and
   wherein said elongated tube has a conduit formed therein through which an electrical current is passed to said germicidal light source.

2. A tube for insertion into a trachea as described in claim 1, wherein said germicidal light source is a plurality of light emitting diodes.

3. A tube for insertion into a trachea as described in claim 2, wherein said light emitting diodes form an annular ring around said elongated tube.

4. A tube for insertion into a trachea as described in claim 2, wherein said light emitting diodes are secured to said elongated tube by a substantially transparent material.

5. A tube for insertion into a trachea as described in claim 2, wherein said light emitting diodes transmit ultraviolet radiation to an exterior surface of said expandable cuff that is outside of said elongated tube.

6. A tube for insertion into a trachea as described in claim 1, further comprising
   a chamber located on said elongated tube and above said expandable cuff, and surrounding at least a portion of said elongated tube, and
   wherein a surface of said chamber that is on an exterior portion of said elongated tube is substantially transparent to said germicidal light; and
   wherein said germicidal light source is present within said chamber, and said germicidal light source transmits germicidal light through said surface of said chamber that is substantially transparent to said germicidal light, and toward said expandable cuff.

7. A tube for insertion into a trachea as described in claim 6, wherein said chamber is an annular chamber, and all exterior surfaces of said annular chamber are smooth.

8. A tube for insertion into a trachea as described in claim 1, wherein said germicidal light source transmits ultraviolet radiation.

9. A tube for insertion into a trachea as described in claim 1, wherein said germicidal light source is mounted to said elongated tube.

10. A tube for insertion into a trachea as described in claim 1, further comprising
    a chamber that is located on said elongated tube and above said expandable cuff, and wherein a surface of said chamber that is on an exterior portion of said elongated tube is substantially transparent to said germicidal light; and
    wherein said light source is an ultraviolet light source that is present within said chamber, and said light source transmits germicidal light through said surface of said chamber that is substantially transparent to said germicidal light, and toward said expandable cuff.

11. A tube for insertion into a trachea as described in claim 1, wherein said germicidal light source transmits germicidal light to a trachea of a user.

12. A tube for insertion into a trachea as described in claim 1, wherein said germicidal light source transmits germicidal light to a portion of said expandable cuff that is outside of said elongated tube.

13. A tube for insertion into a trachea as described in claim 1, the tube for insertion into the trachea further comprising a timing circuit, wherein when the tube for insertion into the trachea is positioned in the trachea, said germicidal light source intermittently transmits germicidal light.

14. A tube for insertion into a trachea, said tube comprising:
    an elongated tube;
    an expandable cuff located on a section of said elongated tube that is expanded to hold said tube within a trachea of a user;
    a germicidal light source that transmits germicidal light to a trachea of a user;
    a chamber that is located on said elongated tube and above said expandable cuff,
    wherein a surface of said chamber that is on an exterior portion of said elongated tube is substantially transparent to said germicidal light, and
    wherein said germicidal light source is present within said chamber, and said germicidal light source transmits said germicidal light through said surface of said chamber that is substantially transparent to said germicidal light and to an exterior of said chamber.

15. A tube for insertion into a trachea as described in claim 14, wherein said germicidal light source transmits germicidal light to a portion of said expandable cuff that is outside of said elongated tube.

* * * * *